United States Patent [19]

Bogdanovic et al.

[11] Patent Number: 5,091,536

[45] Date of Patent: Feb. 25, 1992

[54] SOLUBLE MAGNESIUM HYDRIDES, METHOD OF PREPARING THEM, AND USE THEREOF

[75] Inventors: Borislav Bogdanović; Manfred Schwickardi, both of Mülheim/Ruhr, Fed. Rep. of Germany

[73] Assignee: Studiengesellschaft Kohle mbh, Mulheim/Ruhr, Fed. Rep. of Germany

[21] Appl. No.: 153,857

[22] Filed: Feb. 9, 1988

[30] Foreign Application Priority Data

Jul. 11, 1987 [DE] Fed. Rep. of Germany ....... 3722993

[51] Int. Cl.$^5$ .................. C07D 221/02; C07F 3/02; C07F 5/06; C07F 5/02
[52] U.S. Cl. ........................ 546/112; 260/665 R; 260/665 G; 568/6; 568/583; 568/671; 568/704; 556/170; 556/175; 556/176; 556/181; 556/182; 564/8; 564/9; 564/10; 564/305; 564/336; 564/355; 564/463; 564/503; 564/508; 564/509; 564/511
[58] Field of Search ............... 423/647, 644, 497; 260/665 R, 665 G; 546/112; 556/170, 175, 176, 181, 182; 564/8, 9, 10, 305, 336, 355, 463, 503, 508, 509, 511; 568/6, 583, 671, 704

[56] References Cited

U.S. PATENT DOCUMENTS

| | | | |
|---|---|---|---|
| 618,645 | 4/1901 | Faust et al. | 423/647 |
| 2,392,545 | 1/1940 | Pechet | 423/647 |
| 3,030,184 | 4/1962 | Faust et al. | 423/647 |
| 3,617,218 | 11/1971 | Tameler | 423/647 |
| 3,666,416 | 5/1972 | Henle et al. | 423/647 |
| 4,554,152 | 11/1985 | Bogdanovic | 423/647 |
| 4,555,395 | 11/1985 | Sirovich et al. | 252/188.26 |

FOREIGN PATENT DOCUMENTS

| | | | |
|---|---|---|---|
| 0112548 | 7/1984 | European Pat. Off. | 423/647 |
| 2804445 | 8/1979 | Fed. Rep. of Germany | 423/647 |
| 717261 | 10/1966 | Italy | 423/647 |
| 6706848 | 11/1967 | Netherlands | 423/647 |

OTHER PUBLICATIONS

Wiberg et al., "Magnesium Hydride", Chemical Abstract 4591.
"Process for Production of Magnesium Hydrides".

Primary Examiner—Paul F. Shaver
Attorney, Agent, or Firm—Sprung, Horn, Kramer & Woods

[57] ABSTRACT

Organic-solvent soluble magnesium hydrides of the formulas $$(MgH_2)_n \cdot MgQ_2 \quad \text{(II)}$$

$$(MgH_2)_n \cdot RMgX \quad \text{(III)}$$

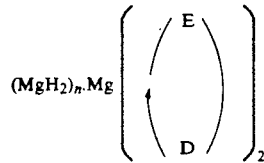

(IV)

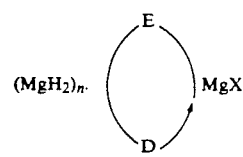

(V)

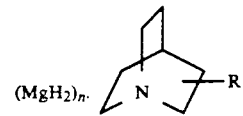

(VI)

$$(MgH_2)_n \cdot MQ_mX_{3-m} \quad \text{(VII)}$$

and

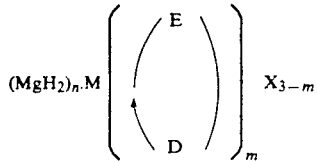
(VIII)

are prepared by catalytically hydrogenating finely powdered magnesium, optionally in the presence of a magnesium halide, in an organic solvent in the presence of their MgH$_2$-free counterparts in which Q is an alkyl, alkenyl, alkoxy, dialkylamide, aralkyl, aryl or diarylamide group, each with up to 18 carbon atoms, R is an alkenyl, aralkyl or aryl group, each with up to 18 carbon atoms, X is chlorine, bromine, or iodine, —E⌢D— is a chelating ligand, E is —CH$_2$, —N(R)— or —O—, ⌢ is an alkylene radical of the formula —(CH$_2$)$_p$, D is a dialkylamide, diarylamide or alkoxy group, each with up to 18 carbon atoms, M is aluminum or boron, m is 1, 2, or 3, and $1 < n \leq 50$.

6 Claims, No Drawings

SOLUBLE MAGNESIUM HYDRIDES, METHOD OF PREPARING THEM, AND USE THEREOF

The present invention relates to previously unknown highly reactive and soluble magnesium hydrides, a method of preparing them, and their use in chemical syntheses.

Magnesium dihydride, MgH$_2$ (hereinafter "magnesium hydride") is known as a solid that is insoluble in all organic and inorganic solvents. This is true not only of the magnesium hydride obtained from the elements at high temperatures and pressures (Ullmans Enzyklopädie der technischen Chemie, 4th Ed., Vol. 13, p. 116) but also of that highly reactive obtained catalytically under mild conditions (B. Bogdanovic, EP 3564, Studiengesellschaft Kohle mbH., 1982).

According to European Patent 3564, hydridomagnesium halides that are soluble in tetrahydrofuran (THF) can be prepared by catalytically hydrogenating magnesium in the presence of magnesium halides. It accordingly becomes possible to prepare tetrahydrofuran solutions for example that are no more than 1.5 molar in terms of the hydride content, assuming the structural formula I (1<n<2) for the dissolved species (B. Bogdanovic & M. Schwickardi, Zeitschrf. f. Naturforsch. 39b (1984), 1001). This means that 2 moles of the soluble hydridomagnesium chloride (HMgCl) can be used to obtain in soluble form 1 mole of the per se insoluble magnesium hydride. The hydridomagnesium chloride solutions can then be concentrated to obtain solutions of Type I with n a maximum of 3.

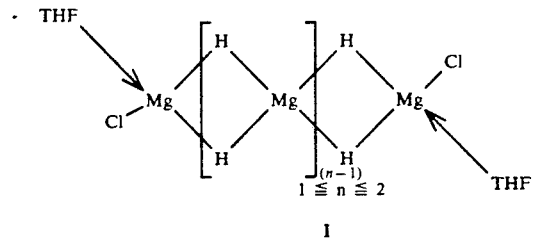

I

It is of course possible to prepare the THF solutions of Type I only at the cost of low hydrogenation temperatures (0° C.), long hydrogenation times (18-20 hours), and incomplete conversion, which is a considerable drawback on an industrial scale.

It is known from the literature that soluble magnesium hydrides of the formula HMgQ—wherein Q is an alkyl, aryl, dialkyl (or aryl) amide, alkoxy, or halide radical—can be obtained by reacting an especially reactive form of magnesium hydride (MgH$_2$*), obtainable from dialkylmagnesium compounds and LiAlH$_4$, by reaction with MgQ$_2$ compounds (E. C. Ashby & T. Smith, Chem. Comm. 30 [1978] for alkyl and aryl; E. C. Ashby et al, J. Org. Chem. 43 [1978], for amide; and E. C. Ashby & A. B. Goel, Inorg. Chem. 18 [1979], 1306 for alcoholate and 16 [1977], 2941 for halide). Thus

and

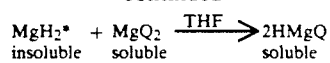

None of the aforesaid instances resulted in the dissolution of more than 1 mole of MgH$_2$* per mole of MgQ$_2$, meaning that solutions of Type II, n>1,

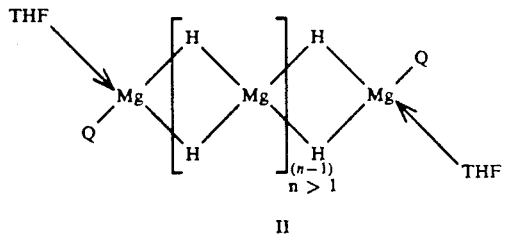

II cannot be obtained in this way, and the method is not appropriate for obtaining soluble MgH$_2$ hydrides on a technical scale.

Even the conversion of a stoichiometric excess of the active magnesium hydride (MgH$_2$), insoluble in tetrahydrofuran, catalytically obtained as described in European Patent 3564 with different MgQ$_2$ compounds in tetrahydrofuran, does not lead to compounds of Type II with n>1. The most that can be obtained is to bring an equimolar amount of MgH$_2$ per mole of MgQ$_2$ into solution. Thus

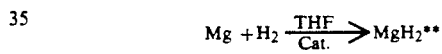

and

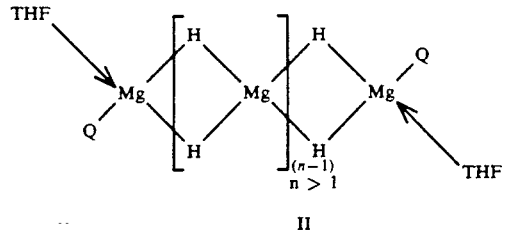

II

It is accordingly an object of the present invention to provide magnesium hydrides (MgH$_2$) that are soluble in the organic phase and a method of preparing them. The desired magnesium hydrides should, due to their satisfactory solubility in the organic phase, have a reactivity as good or better than magnesium hydrides from the state of the art 2 and should also be stable for a long time when dissolved, with no loss of reactivity. The object also includes providing magnesium hydrides that are much easier to handle and especially to measure out than the known solid magnesium hydrides. The method should also make available such organic-soluble magnesium hydrides in yields appropriate for industrial-scale production.

It has now surprisingly been discovered that highly active magnesium hydrides (MgH$_2$) can be prepared in a soluble form by preparing adducts of magnesium hydride on organomagnesium compounds, organoboron compounds, organoaluminum compounds, or even tertiary bicyclic amines. The preparation of such adducts leads, surprisingly even on an industrial scale, to highly active magnesium hydrides that are soluble in organic phase.

The invention relates to magnesium hydrides that are soluble in the organic phase and have the general formulas $(MgH_2)_n \cdot MgQ_2$      (II)

$(MgH_2)_n \cdot RMgX$      (III)

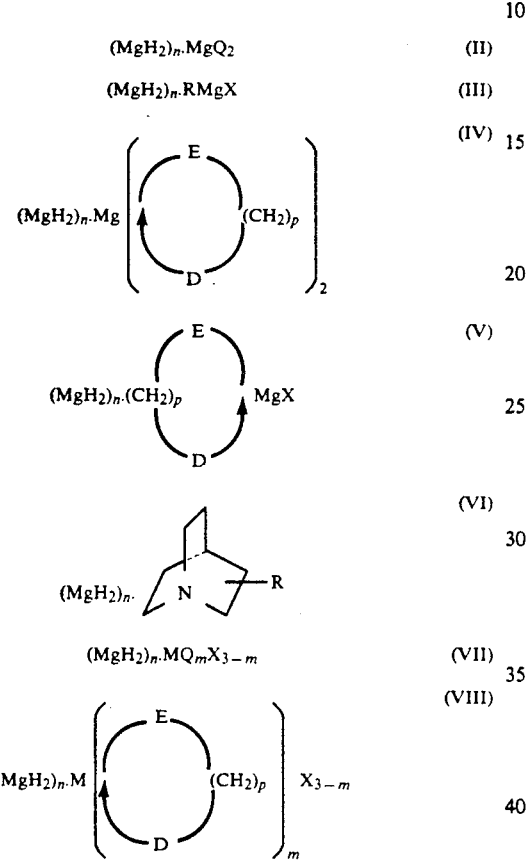

(IV)

(V)

(VI)

$(MgH_2)_n \cdot MQ_mX_{3-m}$      (VII)

(VIII)

wherein

Q represents straight-chained or branched alkyl, alkenyl, alkoxy, dialkylamide, aralkyl, aryl or diarylamide groups with 1 to 18 carbon atoms in the alkyl group and 6 to 18 carbon atoms in the aryl group, R represents alkyl, alkenyl, aralkyl, or aryl groups with comparable numbers of atoms, X is chlorine, bromine, or iodine,

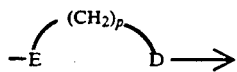

is a chelating ligand wherein E is —CH$_2$—, —N(R)— and —O—, and D represents a dialkylamide, diarylamide or alkoxy group with comparable numbers of carbon atoms, p is a whole number from 1 to 6, M is aluminum or boron, $1 < n \leq 50$, and m is 1, 2, or 3.

The invention also relates to a method of preparing soluble magnesium hydride of the general formulas (II) through (VIII) characterized by catalytically hydrogenating finely powdered magnesium, optionally in the presence of magnesium halides, in an organic solvent in the presence of the compounds $MgQ_2$      (IIa)

$RMgX$      (IIIa)

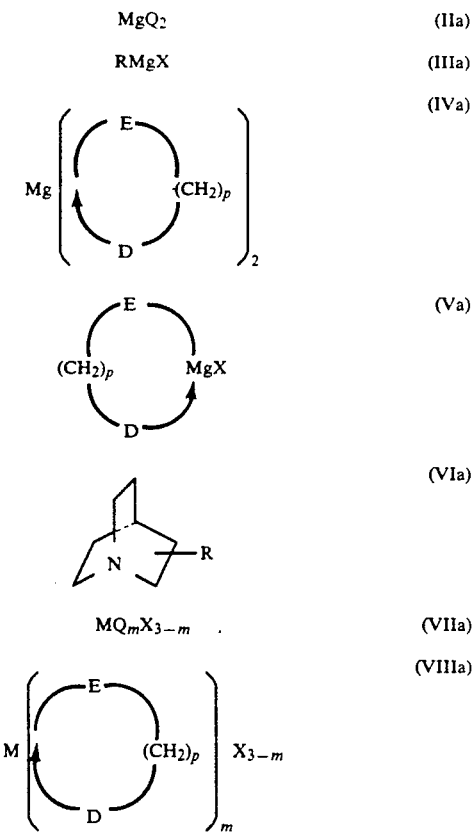

(IVa)

(Va)

(VIa)

$MQ_mX_{3-m}$      (VIIa)

(VIIIa)

wherein Q, R, X, —E⌒D→, M, and m have the foregoing significance.

The invention also relates to the use of soluble magnesium hydrides of Formulas II through VIII, wherein Q, R, X,

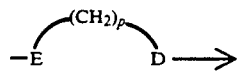

p, M, m, and n have the foregoing significance, to prepare organomagnesium compounds as reducing agents and as reagents for hydrogenating metals and non-metals.

The new magnesium hydrides that are soluble in the organic phase in accordance with the invention have the general formulas II through VIII, wherein Q represents straight-chained or branched alkyl, alkenyl, alkoxy, dialkylamide, aralkyl, aryl or diarylamide groups with 1 to 18 carbon atoms in the alkyl group and 6 to 18 carbon atoms in the aryl group. The n-alkyl groups accordingly include the series methyl, ethyl, propyl, butyl, pentyl, hexyl, heptyl, octyl, nonyl, decyl, undecyl, dodecyl, tridecyl, tetradecyl, pentadecyl, hexadecyl, heptadecyl, and octadecyl. Instead of the aforesaid n-alkyl groups, Q can also represent their branched-chain isomers with 1 to 18 carbon atoms. How many branches the alkyl has or at what points in the chain they occur makes no difference. Alkyls with 1 to 8 carbon atoms are preferred.

Instead of the alkyl groups, the Q in Formulas II and VII can represent alkenyl groups with 1 to 18 carbon atoms. These can also be straight-chained or branched and have one or more double bonds at any point on the chain or side chain. An alkenyl with 1 to 8 carbon atoms is preferred. One example is the allyl group.

The Q in the aforesaid general formulas can also stand for alkoxy groups with 1 to 18 carbon atoms in the alkyl. Any of the alkyl groups previously specified herein can also contain a hydroxy substituent, preferably at the terminal carbon atom. The preferred alkoxy groups that Q can represent are those with 1 to 6 carbon atoms.

The Q in the aforesaid formulas can also stand for aralkyl or aryl groups with comparable numbers of carbon atoms. Preferred are benzyl, phenylethyl and phenyl. Q as even higher aralkyl or aryl groups, however, is also possible in the general formulas II and VII.

Q can also stand for dialkylamide or diarylamide groups with comparable numbers of carbon atoms. Groups of this type have two alkyls or aryls of the previously specified series attached to their amide-nitrogen atom.

The R in general formulas III and VI stands for straight-chain or branched alkyl or alkenyl groups or aralkyl or aryl groups with numbers of carbon atoms that are comparable to those of the aforesaid Q groups. Especially preferred from the aforesaid series for R are straight-chain alkyls with 1 to 8 carbon atoms, allyl, benzyl or phenyl radicals.

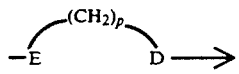

in the general formulas IV, V, and VIII stands for chelating ligands wherein E represents —CH$_2$—, —N(R)— or —O—, D represents a dialkylamide, diarylamide or alkoxy group, all from the previously specified series, and is an alkylene group from the series methylene, ethhexamethylene. E and D are accordingly attached through an alkylene of that type.

n in the aforesaid Formulas II through VIII can be greater than 1 and less than or equal to 50. This means that more than 1 but no more than 50 molecules of magnesium hydride (MgH$_2$) per molecule of the adductor are bonded in the compounds with the general formulas II through VIII in accordance with the invention. The structure of these compounds should essentially be depicted as previously herein in relation to the hydride magnesium halides I or the 1:1 adducts of the organomagnesium hydrides II.

The compounds of the general formulas II through VIII are prepared in accordance with the invention by catalytically hydrogenating finely powdered magnesium in an organic solvent in the presence of the compounds IIa through VIIIa. The finely powdered magnesium is commercially available powdered magnesium obtained by technical synthesis. It will preferably have a particle size of 0.3 to 0.04 mm (50-325 mesh). Such finely powdered magnesium is listed for example on page 7 of the catalog of the Ventron Company (1983).

The reaction is carried out in an appropriate organic solvent. Preferred solvents are those that stabilize alkaline earth metals in the organic phase. Particularly appropriate are cyclic ethers, preferably tetrahydrofuran.

The catalytic hydrogenation is carried out in the presence of slight amounts of compounds IIa through VIII a. In the context of the aforesaid definitions of Q, R, X,

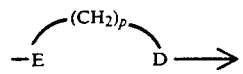

M, and m, diorganomagnesium compounds, organomagnesium halides, bis(chelate)magnesium compounds, chelatemagnesium halides, quinuclidine or its organosubstituted homologues, which can be substituted with an R of the aforesaid series at any point of the bicyclic ring system, aluminum trialkyls, aluminumalkyl halides, boron trialkyls, boronalkyl halides, and aluminum-chelate halides or boronchelate halides are appropriate.

The catalytic hydrogenation is carried out with molecular hydrogen, which is supplied to the system in a conventional way at normal or elevated pressure. Operating at an elevated molecular-hydrogen pressure of up to 60 bars is preferred.

Preferred catalysts are those described in European Patent 3564 and European Laid Open Application 157,297. This means halides of the metals of the IVth through VIII subgroups of the periodic system. Especially preferred are compounds or combinations of compounds from the halides of titanium, chromium and iron. Usually supplied to the system as co-catalysts are such polycyclic aromatics as anthracene or its magnesium adduct (magnesium anthracene).

It is also possible to add equimolar or preferably substoichiometric (catalytic) amounts of magnesium halides (MgX$_2$) during the hydrogenation. Such magnesium halides however, are, like the extra tertiary amine described as a co-catalyst in the aforementioned publications, unnecessary, although they can have a positive effect on the yield and purity of the reaction product.

The soluble magnesium hydrides II through VIII are formed in accordance with the reaction equations

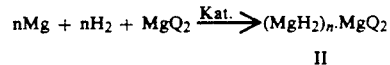

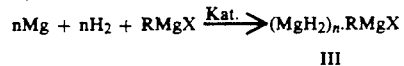

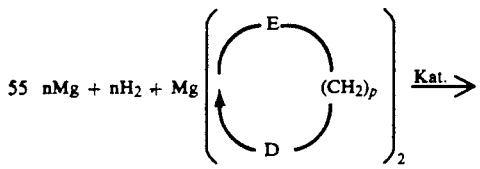

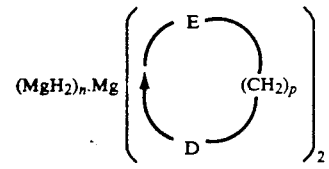

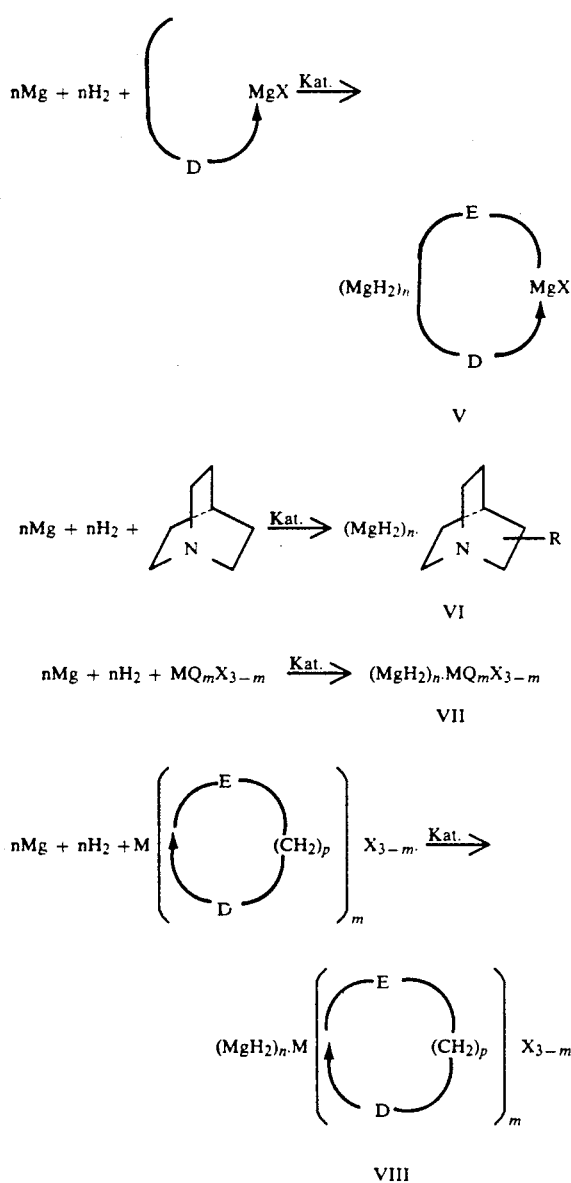

V

VI

VII

VIII

In one preferred embodiment of the method in accordance with the invention it is possible to produce the reaction components RMgX (IIIa) or

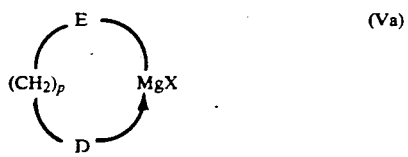

(Va)

in situ from magnesium and RX or from the chelating ligand

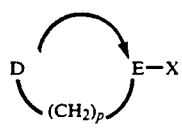

instead of adding it already synthesized to the reaction batch to prepare compounds III or V.

The soluble magnesium hydrides prepared in accordance with the instant method can be used for, among other purposes, preparing organomagnesium compounds by adding them to 1-alkenes, as reducing agents, and to prepare metallic or elementary hydrides (SiH$_4$) and intermetallic compounds and their hydrides and carbides (J. of the Less Common Metals 131 [1987], 163). They have the following advantages over the catalytically prepared suspensions and solid magnesium hydride:

Easy and safe handling and transportation in that the up-to-5 molar solution in tetrahydrofuran does not, in contrast to the suspension, ignite in air.

Higher reactivity in chemical reactions.

Better possibility for measuring out.

The stability of the MgH$_2$ solutions in tetrahydrofuran at room temperature depends on the molarity and the type of complexing agent. Whereas it was possible to keep a solution with the composition (MgCl$_2$)$_6$·Mg(C$_8$H$_{17}$)$_2$·(MgCl$_2$)$_{0.3}$(3.8 molar in terms of the MgH$_2$) under argon for 4 weeks with a practically unaltered hydride concentration, a solution with the composition (MgH$_2$)$_{30}$·n-C$_8$H$_{17}$MgCl (3.7 molar in terms of the MgH$_2$) solidified after only one week at room temperature. Evaporating the tetrahydrofuran in vacuum from a solution of MgH$_2$ in tetrahydrofuran with the composition (MgH$_2$)$_{6.5}$·Mg(n-C$_8$H$_{17}$)$_2$·(MgCl$_2$)$_{0.7}$ (1.9 molar in terms of the MgH$_2$) yielded a viscous oil that it was possible to re-dissolve in the same volume of tetrahydrofuran to obtain the same hydride content.

The process will now be described with reference to examples which are not to be considered as limiting the scope of the invention in any way.

EXAMPLE 1

The reaction vessel was a 250 ml two-necked cylindrical flask equipped with a magnetic stirrer, a tailkey stopcock, and stoppers, and was an appropriate glass insert for a 50 ml autoclave. 10.00 g (411 mmoles) of powdered magnesium (with a mean particle size of 0.050 mm or appr. 270 mesh) and 0.73 g (4.1 mmoles) of anthracene were added to 20 ml of absolute tetrahydrofuran. 0.05 ml of ethyl bromide were added and the suspension was stirred at room temperature. The solution turned green, and orange magnesium anthracene tetrahydrofuran precipitated out about 20 minutes later. 0.72 g (4.5 mmoles) of anhydrous CrCl$_3$ was added to the batch, which was simultaneously cooled (with water at 15° C.) and stirred, whereupon magnesium anthracene went into solution in an exothermic reaction accompanied by a color change to deep brown. The solution was then treated with, first, 30 ml of tetrahydrofuran and, in tetrahydrofuran (26 mmoles) (B. Bogdanovic, M. Schwickardi, & P. Sikorski, Angew. Chem. Suppl. [1982], 457). The glass vessel was placed in a flat-bottomed 500 ml stainless steel autoclave and the suspension hydrogenated while simultaneously being powerfully agitated with the magnetic stirrer at 22° to 26 ° C. and an initial hydrogen pressure of 60 bar. The hydrogen pressure dropped to 40 bar within 3¾ hours. The volume of the resulting magnesium hydride mixture was 77 ml. 10 ml was centrifuged for 1 hour at 10 000 rpm. 2.0 ml of the clear residual solution was subjected to protolysis with ethanol (cooled with water), yielding 318 ml of gas (20° C. at 1 bar) composed (by MS analysis) of $H_2$ 97.6, $C_2H_5OH$ 1.8, and THF 0.6% (another sample of the solution was centrifuged for 2.5 hours with the same result). The amount of $H_2$ that formed was equivalent to a total magnesium hydride in solution of 249 mmoles or a yield of 61% soluble magnesium hydride in terms of the initial powdered magnesium. The composition of the soluble magnesium hydride is determined from the amount of di-n-octylmagnesium employed (26 mmoles) to be $(MgH_2)_{9.6} \cdot Mg(n-C_8H_{17})_2$. The concentration of the tetrahydrofuran solution was 3.25 molar in terms of the soluble magnesium hydride. IR analysis of a centrifuged magnesium-hydride solution revealed the broad absorption band at 1100 cm$^{-1}$ typical of $MgH_2$ and another magnesium-hydride band at 670 cm$^{-1}$.

EXAMPLES 2 to 17

These tests were carried out analogously to Example 1 and with the same amounts of magnesium, anthracene, $CrCl_3$, and tetrahydrofuran. The details and results of the tests are listed in Table 1. Example 17 was a comparison example, with no complexing agents.

TABLE 1

Preparing soluble magnesium hydrides by catalytically hydrogenating magnesium in the presence of various complexing agents (see text for amounts)

| Ex. No. | $MgCl_2^a$ added | Complexing agent mmoles/ml THF | Hydr. time, hours | Pressure$^b$ drop, bar | Vol. of susp. ml | Vol. $H_2^c$ from protol. ml |
|---|---|---|---|---|---|---|
| 1 | — | $Mg(n-C_8H_{17})_2$ 26/22 | 3.75 | 20 | 77 | 310 |
| 2 | + | $Mg(CH_3C_6H_5)_2$ 26/20 | 2.5 | 25 | 72 | 343 |
| 3 | — | $n-C_8H_{17}MgCl$ 18/15 | 4.5 | 24 | 76 | 345 |
| 4 | — | $n-C_8H_{17}MgCl$ 9/8 | 5.33 | 23 | 75 | 359 |
| 5 | — | $n-C_8H_{17}Cl^e$ 20/— | 3.66 | 23 | 77 | 307 |
| 6 | — | $nC_4H_9MgCl$ 18/14 | 4.25 | 23 | 72 | 236 |
| 7 | + | $Mg[(CH_2)_4OCH_3]_2$ 20/10 | 1 | 11 | 64 | 196 |
| 8 | — | $Cl(CH_2)_3OCH_3^e$ 25/— | 5.66 | 24 | 77 | 361 |
| 9 | — | $Mg[(CH_2)_4OCH_3]_2$ 24/9 | 7.25 | 23 | 75 | 305 |
| 10 | + | $Mg[(CH_2)_3N(CH_3)_2]_2$ 28.4/— | 3.33 | 17 | 75 | 163 |
| 11 | + | $Mg[O(CH_2)_2CH(CH_3)OCH_3]_2$ 26/25 | 6 | 10 | 73$^f$ | 85 |
| 12 | — | $C_7H_{13}N \cdot HCl^g$ 19.6/— | 5 | 22 | 55 | 436 |
| 13 | — | $C_7H_{13}N \cdot HCl^{g,h}$ 5.2/— | 5 | 22 | 100 | 228 |
| 14 | + | $Al(n-C_8H_{17})_3$ 26/20 | 7.5 | 23 | 80 | 237 |
| 15 | + | $Al(n-C_4H_9)_3$ 25/— | 3.5 | 16.5 | 75 | 127 |
| 16 | + | $B(CH_2C_6H_5)_3$ 25/— | 6.75 | 23 | 70 | 169 |
| 17$^i$ | + | — | 3.25 | 22 | 69 | 32 |

| Ex. No. | Hydride content moles H/l | mmoles $MgH_2$ in sol. | Yield$^d$ of sol. $MgH_2$ (%) | Composition of soluble $MgH_2$ |
|---|---|---|---|---|
| 1 | 6.5 | 249 | 61 | $(MgH_2)_{9.6} \cdot Mg(n-C_8H_{17})_2$ |
| 2 | 7.15 | 257 | 63 | $(MgH_2)_{10} \cdot Mg(CH_2C_6H_5)_2 \cdot (MgCl_2)_{0.6}$ |
| 3 | 7.2 | 273 | 66 | $(MgH_2)_{15} \cdot n-C_8H_{17}MgCl$ |
| 4 | 7.5 | 280 | 68 | $(MgH_2)_{30.8} \cdot n-C_8H_{17}MgCl$ |
| 5 | 6.4 | 246 | 63 | $(MgH_2)_{12.3} \cdot n-C_8H_{17}MgCl$ |
| 6 | 4.9 | 177 | 43 | $(MgH_2)_{10} \cdot n-C_4H_9MgCl$ |
| 7 | 4.1 | 130 | 32 | $(MgH_2)_{6.5} \cdot Mg[(CH_2)_4OCH_3]_2 (MgCl_2)_{0.7}$ |
| 8 | 7.5 | 290 | 75 | $(MgH_2)_{11.6} \cdot ClMg(CH_2)_3OCH_3$ |
| 9 | 6.35 | 238 | 58 | $(MgH_2)_{10} \cdot Mg[(CH_2)_4OCH_3]_2$ |
| 10 | 3.4 | 127 | 31 | $(MgH_2)_{4.5} \cdot Mg[(C_3H_6N(CH_3)_2]_2 \cdot (MgCl_2)_{0.5}$ |
| 11 | 1.7 | 64 | 15 | $(MgH_2)_{2.5} \cdot Mg[O(CH_2)_2CH(CH_3)OCH_3]_2 \cdot (MgCl_2)_{0.6}$ |
| 12 | 9.1 | 250 | 62 | $(MgH_2)_{12.7} \cdot C_7H_{13}N \cdot (MgCl_2)_{0.5}$ |
| 13 | 4.7 | 237 | 58 | $(MgH_2)_{46} \cdot C_7H_{13}N \cdot (MgCl_2)_{0.5}$ |
| 14 | 4.9 | 197 | 48 | $(MgH_2)_{7.6} \cdot Al(C_8H_{17})_3 \cdot (MgCl_2)_{0.6}$ |
| 15 | 2.65 | 99 | 24 | $(MgH_2)_4 \cdot Al(C_4H_9)_3 \cdot (MgCl_2)_{0.6}$ |
| 16 | 3.5 | 123 | 30 | $(MgH_2)_{4.9} \cdot B(CH_2C_6H_5)_3 \cdot (MgCl_2)_{0.6}$ |
| 17$^i$ | 0.67 | 23 | 5.6 | $(MgH_2)_{1.5} \cdot MgCl_2$ |

Notes to Table a) 15 mmoles of $MgCl_2$ in 30 ml of tetrahydrofuran, added subsequent to the addition of $CrCl_3$, in each case.

b) The pressure drop is 23 to 24 bar for the quantitative hydrogenation of magnesium.

c) 2.0 ml of the centrifuged solution; ml $H_2$ (20° C./1 bar).

d) Total yield of soluble magnesium hydride (in terms of Mg) due to protolysis.

e) The Grignard bond occurs here in situ from magnesium and alkyl halide, added subsequent to the addition of $CrCl_3$.

f) The solution is highly viscous.
g) Quinuclidine hydrochloride.
h) 2% molar of $CrCl_3$ or anthracene (in terms of the magnesium) were employed in this case.
i) Comparison example without complexing agent.

EXAMPLE 18

The reaction vessel was a 250 ml two-necked cylindrical flask equipped with a magnetic stirrer, a tailkey stopcock, and stoppers, and was an appropriate glass insert for a 50 ml autoclave. 10.00 g (411 mmoles) of powdered magnesium (with a mean particle size of 0.050 mm or appr. 270 mesh) and 0.73 g (4.1 mmoles) of anthracene were added to 20 ml of absolute tetrahydrofuran. 0.05 ml of ethyl bromide were added and the suspension was stirred at room temperature. The solution turned green, and orange magnesium anthracene tetrahydrofuran precipitated out about 20 minutes later. 0.57 g (4.5 mmoles) of anhydrous $FeCl_2$ was added to the batch, which was simultaneously cooled (with water at 15° C.) and stirred, upon which magnesium anthracene went into solution in an exothermic reaction accompanied by a color change to deep brown. The solution was then treated with, first, 40 ml of tetrahydrofuran and, second, 11.8 ml of a 1.74 molar n-octyl-magnesium chloride solution in tetrahydrofuran (20.5 mmoles).

The glass vessel was placed in a flat-bottomed 500 ml stainless-steel autoclave and the suspension hydrogenated while simultaneously being powerfully agitated with the magnetic stirrer at 20° C. and an initial hydrogen pressure of 60 bar. The hydrogen pressure dropped to 40 bar within 4 hours. The volume of the resulting magnesium hydride mixture was 78.5 ml. 10 ml was centrifuged for 1 hour at 10,000 rpm. 2.0 ml of the clear residual solution was subjected to pyrolysis with ethanol (cooled with water), yielding 433 ml of gas (20° C. at 1 bar) composed (by MS analysis) of $H_2$ 95.3, $C_2H_5OH$ 2.8, and THF 1.9%. The amount of $H_2$ that formed was equivalent to a total magnesium hydride in solution of 337 mmoles or a yield of 82% soluble magnesium hydride in terms of the initial powdered magnesium. The composition of the soluble magnesium hydride is determined from the amount of n-octylmagnesium chloride employed to be $(MgH_2)_{16.4}$.n-$C_8H_{17}MgCl$. The concentration of the tetrahydrofuran solution was 4.3 molar in terms of the soluble magnesium hydride.

EXAMPLE 19

The reaction vessel was a 250 ml two-necked cylindrical flask equipped with a magnetic stirrer, a tailkey stopcock, and stoppers, and was an appropriate glass insert for a 50 ml autoclave. 10.00 g (411 mmoles) of powdered magnesium (with a mean particle size of 0.050 mm or appr. 270 mesh) and 0.73 g (4.1 mmoles) of anthracene were added to 20 ml of absolute tetrahydrofuran. 0.05 ml of ethyl bromide were added and the suspension was stirred at room temperature. The solution turned green, and orange magnesium anthracene tetrahydrofuran precipitated out about 20 minutes later. 0.56 g (4.4 mmoles) of anhydrous $FeCl_2$ was added to the batch, which was simultaneously cooled (with water at 15° C.) and stirred, upon which magnesium anthracene went into solution in an exothermic reaction accompanied by a color change to deep brown. The solution was then treated with, first, 10 ml of tetrahydrofuran and, second, 11 ml of a 1.86 molar quinuclidine solution in tetrahydrofuran (20.5 mmoles) and 30 ml of a 0.49 molar $MgCl_2$ solution in tetrahydrofuran (14.7 mmoles).

The glass vessel was placed in a flat-bottomed 500 ml stainless-steel autoclave and the suspension hydrogenated while simultaneously being powerfully agitated with the magnetic stirrer at 20°-26° C. and an initial hydrogen pressure of 60 bar. The hydrogen pressure dropped to 40 bar within 4 hours. The volume of the resulting magnesium hydride mixture was 78 ml. 10 ml was centrifuged for 1 hour at 10,000 rpm. 2.0 ml of the clear residual solution was subjected to pyrolysis with ethanol (cooled with water), yielding 462 ml of gas (20° C. at 1 bar) composed (by MS analysis) of $H_2$ 96.3, $C_2H_5OH$ 2.2, and THF 1.5%. The amount of $H_2$ that formed was equivalent to a total magnesium hydride in solution of 361 mmoles or a yield of 88% soluble magnesium hydride in terms of the initial powdered magnesium. The composition of the soluble magnesium hydride is determined from the amount of quinuclidine employed (20.5 mmoles) to be $(MgH_2)_{17.6}$.quinuclidine. The concentration of the tetrahydrofuran solution was 4.6 molar in terms of the soluble magnesium hydride.

EXAMPLE 20

The reaction vessel was a 250 ml two-necked cylindrical flask equipped with a magnetic stirrer, a tailkey stopcock, and stoppers, and was an appropriate glass insert for a 50 ml autoclave. 10.00 g (411 mmoles) of powdered magnesium (with a mean particle size of 0.050 mm or appr. 270 mesh) and 0.73 g (4.1 mmoles) of anthracene were added to 20 ml of absolute tetrahydrofuran. 0.05 ml of ethyl bromide were added and the suspension was stirred at room temperature. The solution turned green, and orange magnesium antracene.tetrahydrofuran precipitated out about 20 minutes later. 0.59 g (4.7 mmoles) of anhydrous $MnCl_2$ was added to the batch, which was simultaneously cooled (with water at 15° C.) and stirred, upon which magnesium anthracene went into solution in an exothermic reaction accompanied by a color change to deep brown. The solution was then treated with, first, 10 ml of tetrahydrofuran and, second, 11 ml of a 1.86 molar quinuclidine solution in tetrahydrofuran (20.5 mmoles) and 30 ml of a 0.49 molar $MgCl_2$ solution in tetrahydrofuran (14.7 mmoles).

The glass vessel was placed in a flat-bottomed 500 ml stainless-steel autoclave and the suspension hydrogenated for 3 days while simultaneously being powerfully agitated with the magnetic stirrer at 20°-25 ° C. and an initial hydrogen pressure of 60 bar. The hydrogen pressure dropped to 40 bar within 4 hours. The volume of the resulting magnesium hydride mixture was 75 ml. 10 ml was centrifuged for 1 hour at 10,000 rpm. 2.0 ml of the clear residual solution was subjected to pyrolysis with ethanol (cooled with water), yielding 275 ml of gas (20° C. at 1 bar) composed (by MS analysis) of $H_2$ 97.1, $C_2H_5OH$ 2.0, and THF 0.9%. The amount of $H_2$ that formed was equivalent to a total magnesium hydride in solution of 209 mmoles or a yield of 51% soluble magnesium hydride in terms of the initial powdered magnesium. The composition of the soluble magnesium hydride is determined from the amount of quinuclidine employed (20.5 mmoles) to be $(MgH_2)_{10.2}$.quinuclidine. The concentration of the tetrahydrofuran solution was 2.8 molar in terms of the soluble magnesium hydride.

It is understood that the specification and examples are illustrative but not limitative of the present inven-

What is claimed is:

1. A process for preparing a soluble magnesium hydride, comprising catalytically hydrogenating finely powdered magnesium in an organic solvent in the presence of a compound selected from the group consisting of MgQ₂  (IIa)

RMgX  (IIIa)

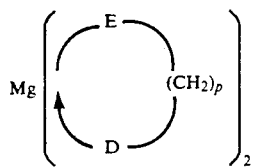  (IVa)

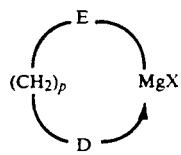  (Va)

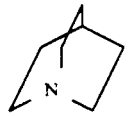  (VIa)

MQ$_m$X$_{3-m}$  (VIIa)

and

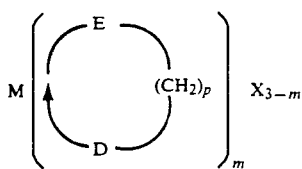  (VIIIa)

in which

Q is an alkyl, alkenyl, alkoxy, dialkylamino, aralkyl, aryl or diarylamino group each with up to 18 carbons, R is an alkenyl, aralkyl or aryl group, each with up to 18 carbon atoms, X is chlorine, bromine, or iodine, $$-E\overset{(CH_2)_p}{\frown}D\rightarrow$$

is a chelating ligand,

E is —CH₂—, —N(R)— or —O—,

D is a dialkylamino, diarylamino or alkoxy group, each with up to 18 carbon atoms, M is aluminum or boron, m is 1, 2, or 3, p is a whole number from 1-6, and 1 ≦ n ≦ 50, or organic solvent dissolving the product as produced.

2. A process according to claim 1, wherein a magnesium halide is also present in the organic solvent during hydrogenation.

3. A process according to claim 1, wherein the powdered magnesium has a mean particle size of 0.04 to 0.3 mm (50 to 325 mesh).

4. A process according to claim 1, wherein the solvent is tetrahydrofuran.

5. A process according to claim 1, wherein the catalyst for the hydrogenation is at least one halide of a metal of the IVth through VIIIth side groups of the periodic system in conjunction with at least one polycyclic aromatic and a magnesium chloride, bromide, or iodide.

6. A process according to claim 5, wherein there is also present a tertiary amine.

* * * * *